(12) United States Patent
Landini et al.

(10) Patent No.: US 10,188,318 B2
(45) Date of Patent: Jan. 29, 2019

(54) BREATH DELIVERY SYSTEM AND METHOD

(75) Inventors: Barbara E. Landini, Mesa, AZ (US);
Joan K. Vrtis, Mesa, AZ (US);
Roberta Druyor-Sanchez, Mesa, AZ (US); Shane Bravard, Phoenix, AZ (US); David Luttrull, Phoenix, AZ (US); James A. McIntyre, Midland, MI (US); Paul E. Cranley, Lake Jackson, TX (US)

(73) Assignee: Invoy Holdings, LLC, Aliso Viejo, CA (US)

( * ) Notice: Subject to any disclaimer, the term of this patent is extended or adjusted under 35 U.S.C. 154(b) by 0 days.

(21) Appl. No.: 13/194,564

(22) Filed: Jul. 29, 2011

(65) Prior Publication Data
US 2012/0071737 A1  Mar. 22, 2012

Related U.S. Application Data

(63) Continuation of application No. 12/263,355, filed on Oct. 31, 2008, now abandoned.

(60) Provisional application No. 61/001,172, filed on Oct. 31, 2007.

(51) Int. Cl.
*A61B 5/097* (2006.01)
(52) U.S. Cl.
CPC .................. *A61B 5/097* (2013.01)
(58) Field of Classification Search
CPC ........................................ A61B 5/097
See application file for complete search history.

(56) References Cited

U.S. PATENT DOCUMENTS

| 4,900,514 A * | 2/1990 | Fuller ............... G01N 33/4972 285/328 |
| 5,908,924 A | 6/1999 | Burdette et al. |
| 6,609,068 B2 | 8/2003 | Cranley et al. |
| 6,858,182 B1 * | 2/2005 | Ito et al. ............... 422/416 |
| 7,364,551 B2 * | 4/2008 | Allen et al. ............... 600/532 |
| 7,794,994 B2 | 9/2010 | Cranley et al. |
| 2002/0124631 A1 | 9/2002 | Sunshine et al. |

(Continued)

FOREIGN PATENT DOCUMENTS

| WO | WO0108554 | 2/2001 |
| WO | WO0128416 | 4/2001 |

OTHER PUBLICATIONS

Byrne, et al. "Evaluation of an Electrochemical Sensor for Measuring Blood Ketones", Emerging Treatments and Technologies Original Article, Diabetes Care, vol. 23, No. 4, dated Apr. 2000, in 4 pages.

(Continued)

*Primary Examiner* — Lore R Jarrett
(74) *Attorney, Agent, or Firm* — Knobbe, Martens, Olson & Bear, LLP

(57) ABSTRACT

Some embodiments of the invention provide a mouthpiece for use with an electronic analyzer for breath analyte detection in an individual. The mouthpiece includes a biosensor and a hydration system. The biosensor includes a chemically active area where a chemical reaction takes place and the hydration system delivers a liquid to the chemically active area of the biosensor to at least one of enhance, enable, and facilitate the chemical reaction. The mouthpiece further includes hardware to transmit breath analyte data.

13 Claims, 7 Drawing Sheets

(56) References Cited

U.S. PATENT DOCUMENTS

| | | | |
|---|---|---|---|
| 2003/0085125 A1 | 5/2003 | Prohaska et al. | |
| 2003/0175993 A1* | 9/2003 | Toranto et al. | 436/518 |
| 2003/0208133 A1 | 11/2003 | Mault | |
| 2003/0224523 A1 | 12/2003 | Thornberg et al. | |
| 2004/0112380 A1* | 6/2004 | Djupesland | A61B 5/085 128/203.12 |
| 2004/0236244 A1* | 11/2004 | Allen et al. | 600/532 |
| 2006/0130557 A1 | 6/2006 | Leddy et al. | |
| 2007/0048180 A1 | 3/2007 | Gabriel et al. | |

OTHER PUBLICATIONS

Dennison, et al. "Direct Monitoring of Formaldehyde Vapour and Detection of Ethanol Vapour Using Dehydrogenase-based Biosensors", Analyst, vol. 121, dated Dec. 1996, in 5 pages.

Kuhn, L. S. "Biosensors: Blockbuster or Bomb? Electrochemical Biosensors for Diabetes Monitoring", The Electrochemical Society, Winter 1998, in 6 pages.

Kundu, et al. "Breath Acetone Analyzer: Diagnostic Tool to Monitor Dietary Fat Loss", Clinical Chemistry, vol. 39, No. 1, dated 1993, in 6 pages.

Landini, B.E. "Breath Acetone Concentration Measured Using a Palm-Size Enzymatic Sensor System", IEEE Sensors Journal, vol. 9, No. 12, dated Dec. 2009, in 6 pages.

Landini, B.E. "Effect of Exhalation Variables on the Current Response of an Enzymatic Breath Acetone Sensing Device", IEEE Sensors Journal, vol. 10, No. 1, dated Jan. 2010, in 6 pages.

Miekisch, et al. "Diagnostic Potential of Breath Analysis—Focus on Volatile Organic Compounds", Elsevier, dated Apr. 2004, in 15 pages.

Pandey, et al. "Ethanol Biosensors and Electrochemical Oxidation of NADH", Analytical Biochemistry 260, Article No. AB982679, dated 1998, in 9 pages.

Park, et al. "Amperometric Biosensor for Determination of Ethanol Vapor", Biosensors & Bioelectronics, vol. 10, pp. 587-594.

* cited by examiner

BREATH DELIVERY SYSTEM AND METHOD

RELATED APPLICATIONS

This application is a continuation of U.S. Nonprovisional application Ser. No. 12/263,355, filed Oct. 31, 2008, which claims priority to U.S. Provisional Application No. 61/001,172, filed Oct. 31, 2007, the contents of which are incorporated herein by reference in their entireties.

BACKGROUND

Current state of the art mouthpieces for drug delivery use liquids in inhalant and nebulizer mouthpieces in order to deliver therapeutic drugs to a user. However, these mouthpieces are only used for drug delivery (i.e., inhaling contents delivered by the mouthpiece) and therefore do not incorporate any type of sensing systems for vapor analysis (e.g., analyzing breath contents exhaled through the mouthpiece).

Some conventional mouthpieces used for vapor analysis (e.g., breath analyte analysis) use a particular breath collection method that requires multiple components. For example, a user exhales into the mouthpiece, a condenser removes breath moisture, and an attached container is used to trap a final breath sample. An analyte biosensor is used for subsequent analyte analysis. The analyte biosensor is either located within the attached container or in a separate piece of analysis equipment that obtains a breath sample from the container. The analyte biosensor chemically reacts with the one or more analytes in the breath sample. The presence of a reaction signifies the presence of the specific analytes, and the strength of the reaction can signify the amount of analyte in the breath sample. The amount of moisture removed from the condenser can be inconsistent and variations due to different mammalian moisture content in the breath can alter the speed and/or strength of the reaction on the analyte biosensor. As none of these mouthpieces incorporate any type of hydration system to create an environment with consistent moisture content for each reaction, results may be inaccurate.

SUMMARY

Some embodiments of the invention provide a mouthpiece for use with an electronic analyzer for breath analyte detection in an individual. The mouthpiece includes a biosensor that detects breath analytes and a hydration system. The biosensor includes a chemically active area where a chemical reaction takes place. The hydration system delivers a liquid to the chemically active area of the biosensor to at least one of enhance, enable, and facilitate the chemical reaction. The mouthpiece further includes an additional sensor capable of detecting additional parameters and hardware to transmit breath analyte data and the additional parameters.

Some embodiments of the invention provide a mouthpiece that includes a biosensor. The biosensor includes a chemically active area where a chemical reaction takes place and is capable of detecting analytes in at least one of breath, saliva, urine, eye vapor, milk and blood. The mouthpiece also includes a hydration system providing liquid to the chemically active area of the biosensor to at least one of enhance, enable, and facilitate the chemical reaction.

Other aspects of the invention will become apparent by consideration of the detailed description and accompanying drawings.

DETAILED DESCRIPTION

Figure 1:
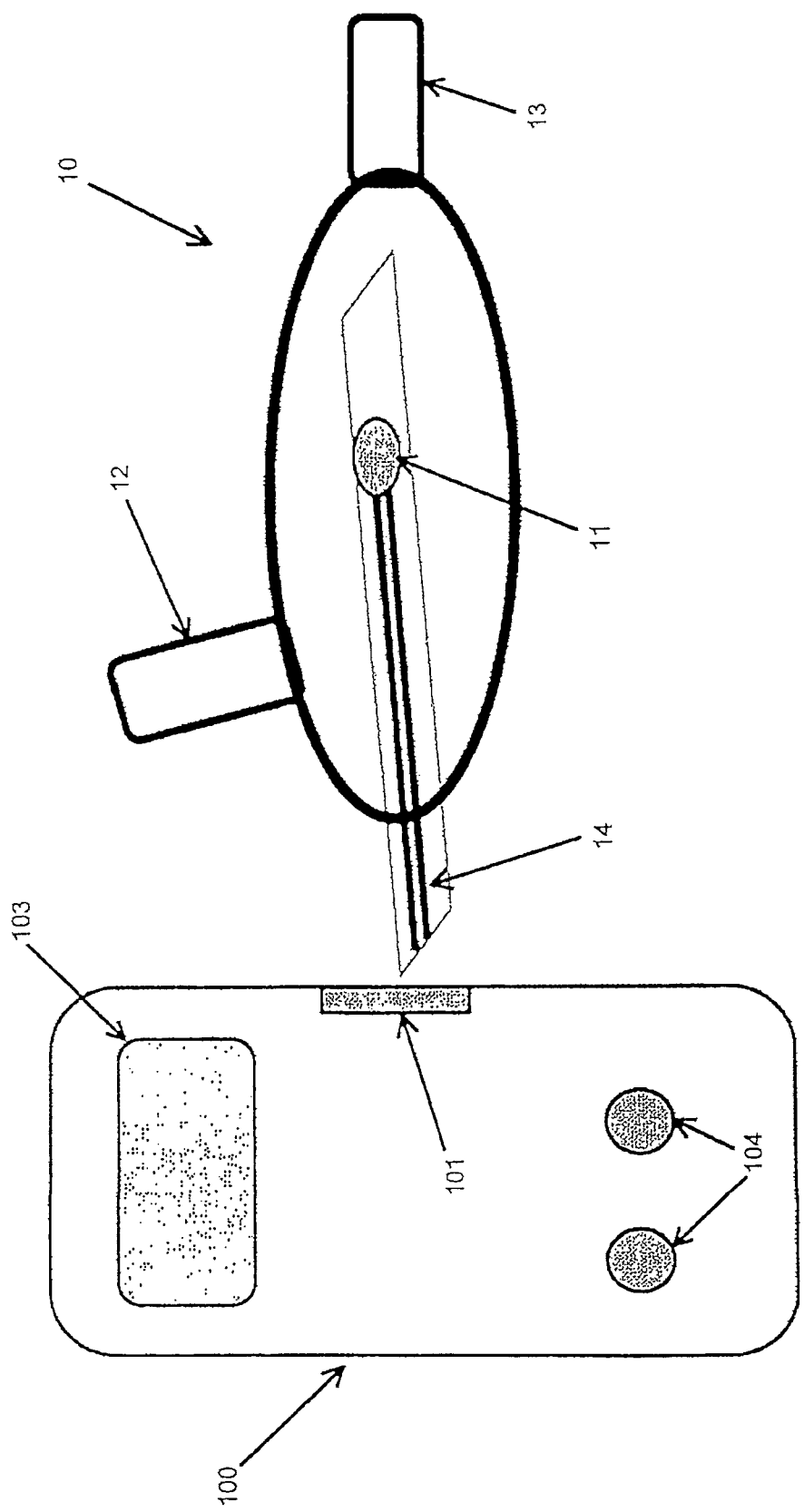
FIGS. 1 & 1A are schematic illustrations of a mouthpiece with an integrated biosensor according to embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIG. 1 illustrates a mouthpiece 10 connected to an electronic analyzer 100, according to some embodiments of the invention. The mouthpiece 10 can be made of a polymer material, such as polyethylene. The mouthpiece 10 can include an integrated biosensor 11, an inlet 12, an outlet 13, and electrical connectors 14. The electrical connectors 14 can connect to an electrical connector receptacle 101 on the electronic analyzer 100. The mouthpiece 10 including the integrated biosensor 11 can be used for the direct detection of breath analytes. The biosensor 11 can include a chemically-active area, such as an area including an enzyme, to permit a chemical reaction when in contact with an analyte. For example, the biosensor 11 can be an enzymatic electrochemical breath acetone sensor. As shown in FIG. 1, the biosensor 11 can be integrated directly into the mouthpiece 10, therefore removing the need for a breath container. The mouthpiece 10 and/or biosensor 11 can be reusable or disposable. The biosensor 11 can be in the form of a sensor strip. During use, an individual can exhale through the inlet 12, causing breath gasses to flow directly over the biosensor 11 and out through the outlet 12. A reaction on the biosensor 11 in response to the breath gasses can take place directly within the mouthpiece 10. In addition, the electrical connectors 14 can transmit analyte data to the electronic analyzer 100 in response to the reaction taking place.

The electronic analyzer 100 can include a display 103 and user interface 104. The electronic analyzer 100 can be a PDA, cell phone, computer, iPod®, or any device capable of receiving, storing, and/or transmitting data from the biosensor 11. Alternatively, the electronic analyzer 100 can be a sensing device specific to the analyte or analytes being detected, such as a breath analyte sensing device for acetone. In various embodiments, the mouthpiece 10 can be mechanically or electrically embedded, or mechanically or electrically integrated into the electronic analyzer 100. In other embodiments, the mouthpiece 10 can include hardware such as a transmitter to transmit data wirelessly to an electronic analyzer 100.

In some embodiments, the biosensor 11 can require a hydration material in order to enable, facilitate, and/or enhance the enzymatic reaction. Variations due to different mammalian moisture content in the breath can alter the speed and/or strength of the reaction. To help provide accurate results with improved precision, the mouthpiece 10 can include an integrated hydration system. The hydration system can provide a consistent amount of hydration material to the biosensor 11 prior to each reaction. The hydration material can be water, an acid, a base, a neutral buffer, a hydrogel, a salt solution, or a liquid containing polymers. The hydration material can depend on the type of biosensor 11. In some embodiments, the viscosity of the hydration material can range from about 0.1 centipoise (cP) to about 200,000 centipoise.

The hydration system can be used to hydrate a dried enzyme on the biosensor 11. The analyte detected by the biosensor 11 can be some kind of volatile, such as acetone in mammalian breath for fat-burn monitoring or volatile organic compounds (VOCs) for disease or cancer detection. Other volatile-carrying mediums, such as vapor or a gas, can be analyzed using the biosensor 11 and the hydration system. Some examples include volatile analyte analysis in animal milk, eye vapor, urine, or mucus. For example, the mouthpiece 10 can act as a chamber containing biosensor 11 with the incorporated hydration system over which vapors from the eye, animal milk, blood, or urine is drawn, for example by a pump.

Figure 1A:
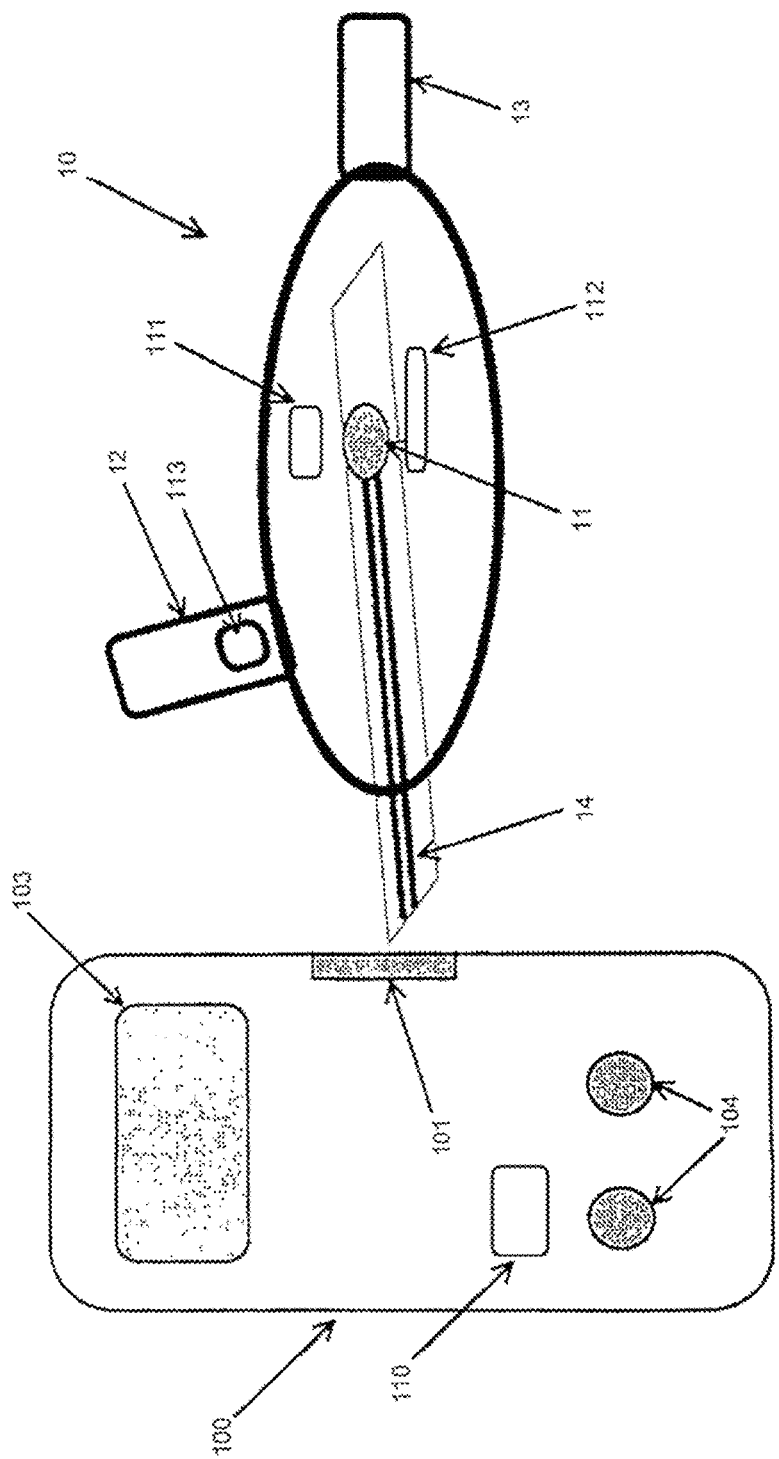

FIG. 1A illustrates a mouthpiece 10 connected to an electronic analyzer 100, according to some embodiments of the invention. The mouthpiece 10 and/or the electronic analyzer 100 shown in FIG. 1A may be similar to the mouthpiece 10 and/or the electronic analyzer 100 shown in FIG. 1. As shown in FIG. 1A, the mouthpiece 10 may include an integrated biosensor, an inlet, an outlet, electrical connectors 14, a liquid sensor 111, a heater 112, and a valve 113. The electronic analyzer 100 may include an electrical connector receptacle 101, a display 103, a user interface 104, and a processor 110.

Figure 2:
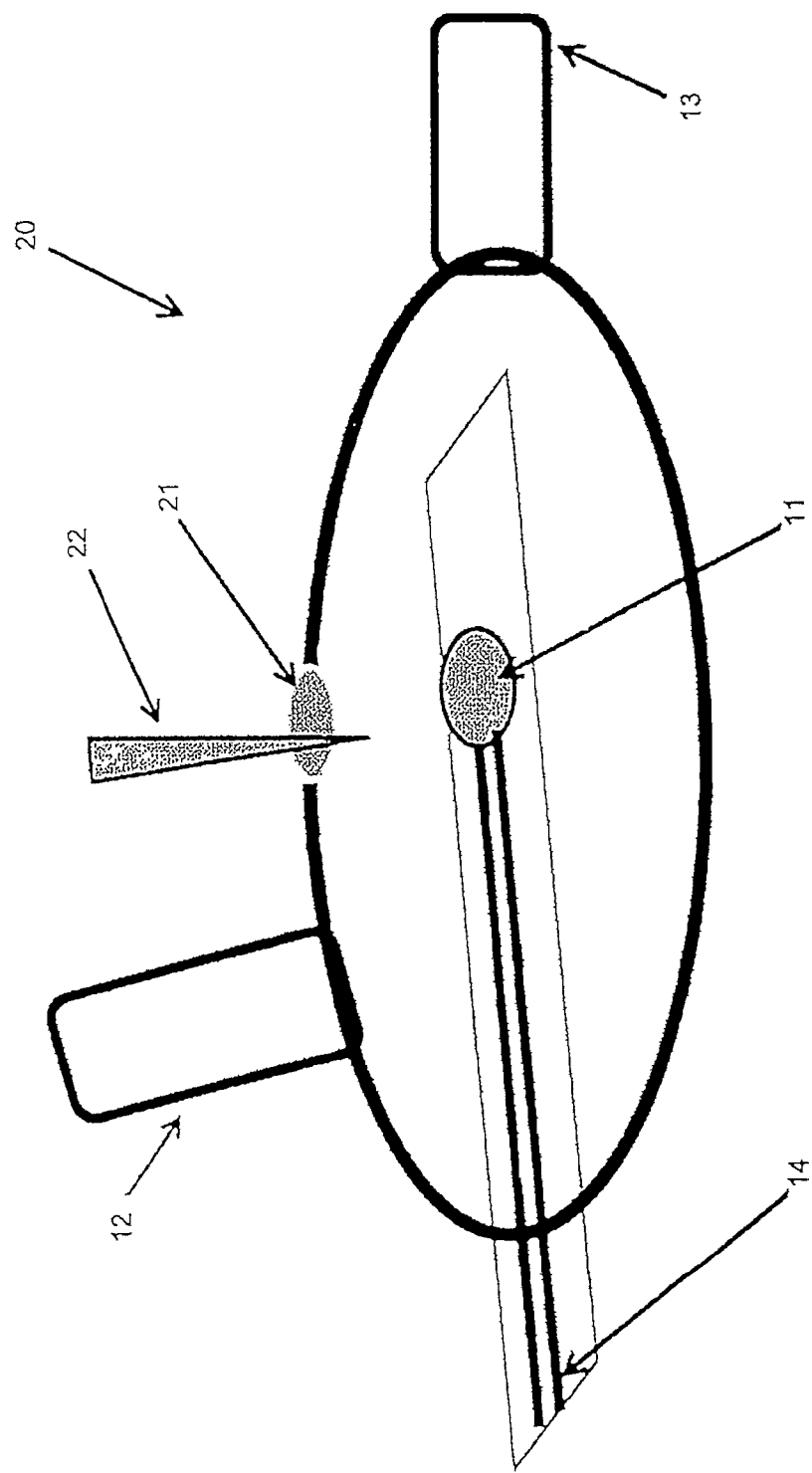
FIG. 2 is a schematic illustration of a mouthpiece with an integrated biosensor with an integrated manual liquid delivery system according to one embodiment of the invention.

In some embodiments, the actuation of the hydration process can be fully manual. For example, FIG. 2 illustrates a reservoir-based hydration system. As shown in FIG. 2, a mouthpiece 20 can include a wetting port 21. The wetting port 21 can be a small hole in the mouthpiece 20 above the biosensor 11. The wetting port 21 can be of a size suitable to allow clearance of a syringe or pipette tip 22. The syringe or pipette 22 can be used to manually wet the biosensor 11 prior to analysis. In some embodiments, the volume range of hydration material can be about 0.05 micro-liters to about 100 micro-liters.

Figure 3:
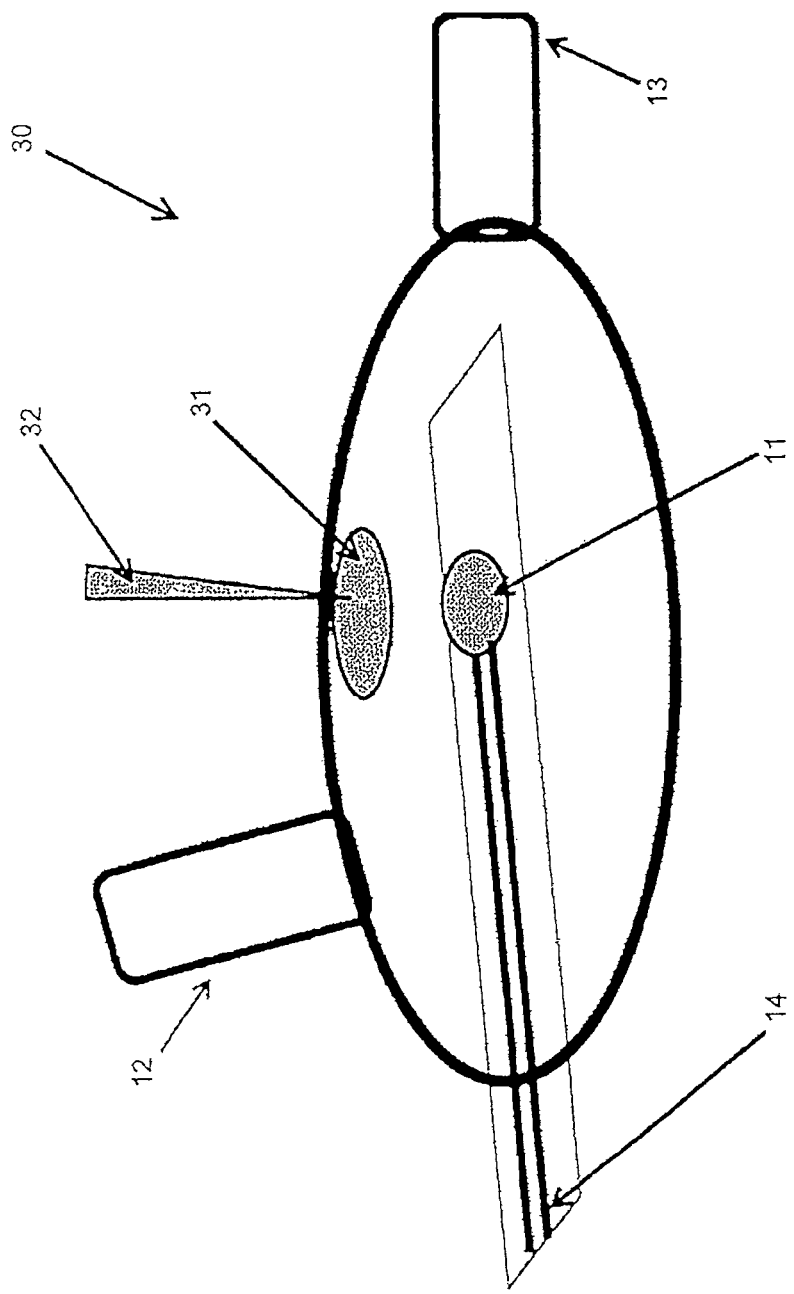
FIG. 3 is a schematic illustration of a mouthpiece with an integrated biosensor with liquid delivery to the biosensor provided by a fluid filled sack according to one embodiment of the invention.

FIG. 3 illustrates a hydration process according to another embodiment of the invention. FIG. 3 illustrates a mouthpiece 30 including a fluid-filled sack 31. The sack 31 (also known as a blister pack) can be housed within the mouthpiece 30 near the biosensor 11 or integrated onto the sensor strip of the biosensor 11. In some embodiments, a pin 32, syringe, or roller can be used to manually pierce or puncture the sack 31 to hydrate the active area of the biosensor 11. In other embodiments, a pushbutton (not shown) on the mouthpiece can include a piercing pin to pierce the sack 31 when the pushbutton is depressed. In other embodiments, the pin 32 or roller can be housed within the mouthpiece 30 and can be depressed to pierce the sack 31 remotely by the electronic analyzer 100 or another electronic device to which the mouthpiece 30 is electrically connected.

Figure 4A:
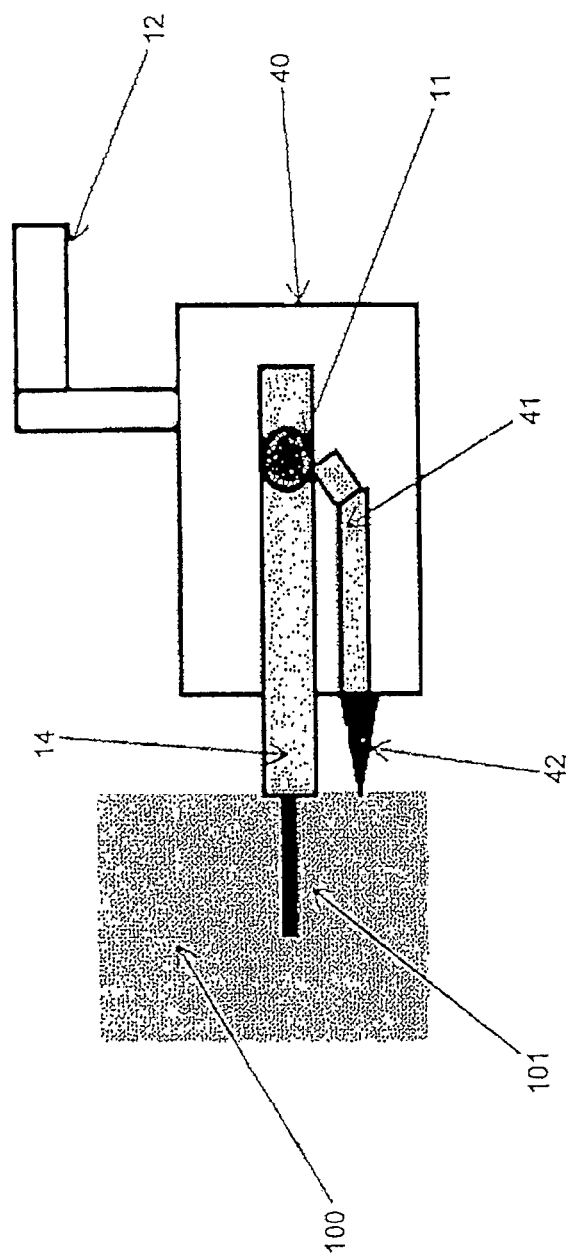
FIGS. 4A and 4B are a schematic illustration and a flow chart of a semiautomatic plunger method of hydration according to one embodiment of the invention.
Figure 4B:
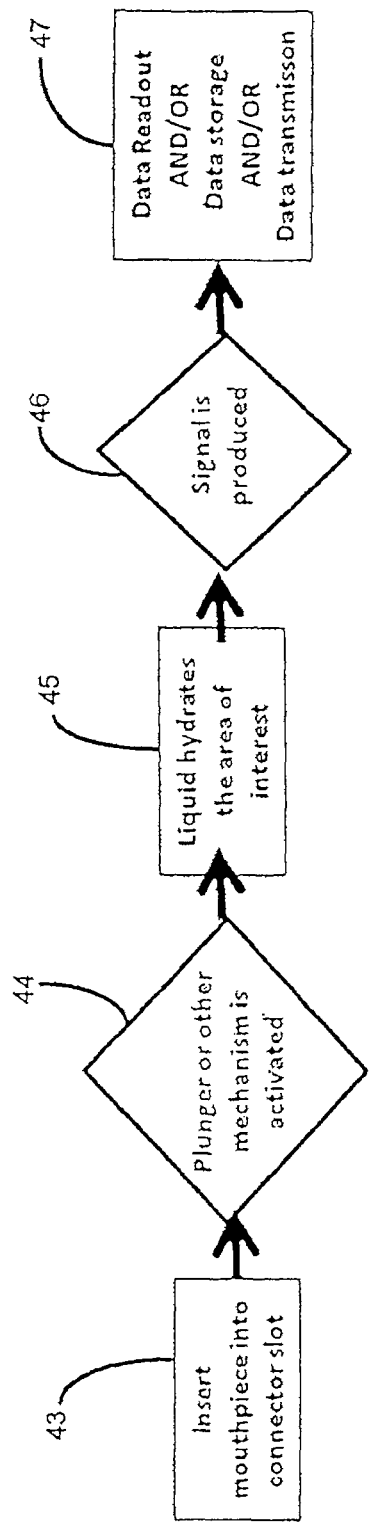

FIGS. 4A-4B illustrate a semi-automatic hydration process according to another embodiment of the invention. FIG. 4A illustrates a mouthpiece 40 including a hydration tube 41 and a plunger 42. FIG. 4B illustrates example method steps for performing the semi-automatic hydration process with the plunger 42. The mouthpiece 40 can be coupled to the electronic analyzer 100 by the electrical connectors 14 (task 43). The plunger 42 can be coupled to the mouthpiece 40 such that coupling the mouthpiece 40 to the electronic analyzer 100 causes the plunger 42 to be depressed (task 44). Once the plunger 42 is depressed, hydration material within the hydration tube 41 hydrates the active area of the biosensor 11 (task 45). A signal can then be produced by the biosensor 11 based on the chemical reaction with an analyte (task 46). The signal can then be transmitted to the electronic analyzer 100 through the electrical connectors 14. Finally, data interpreted from the signal can be displayed, stored, or transmitted by the electronic analyzer 100 (task 47).

Figure 5:
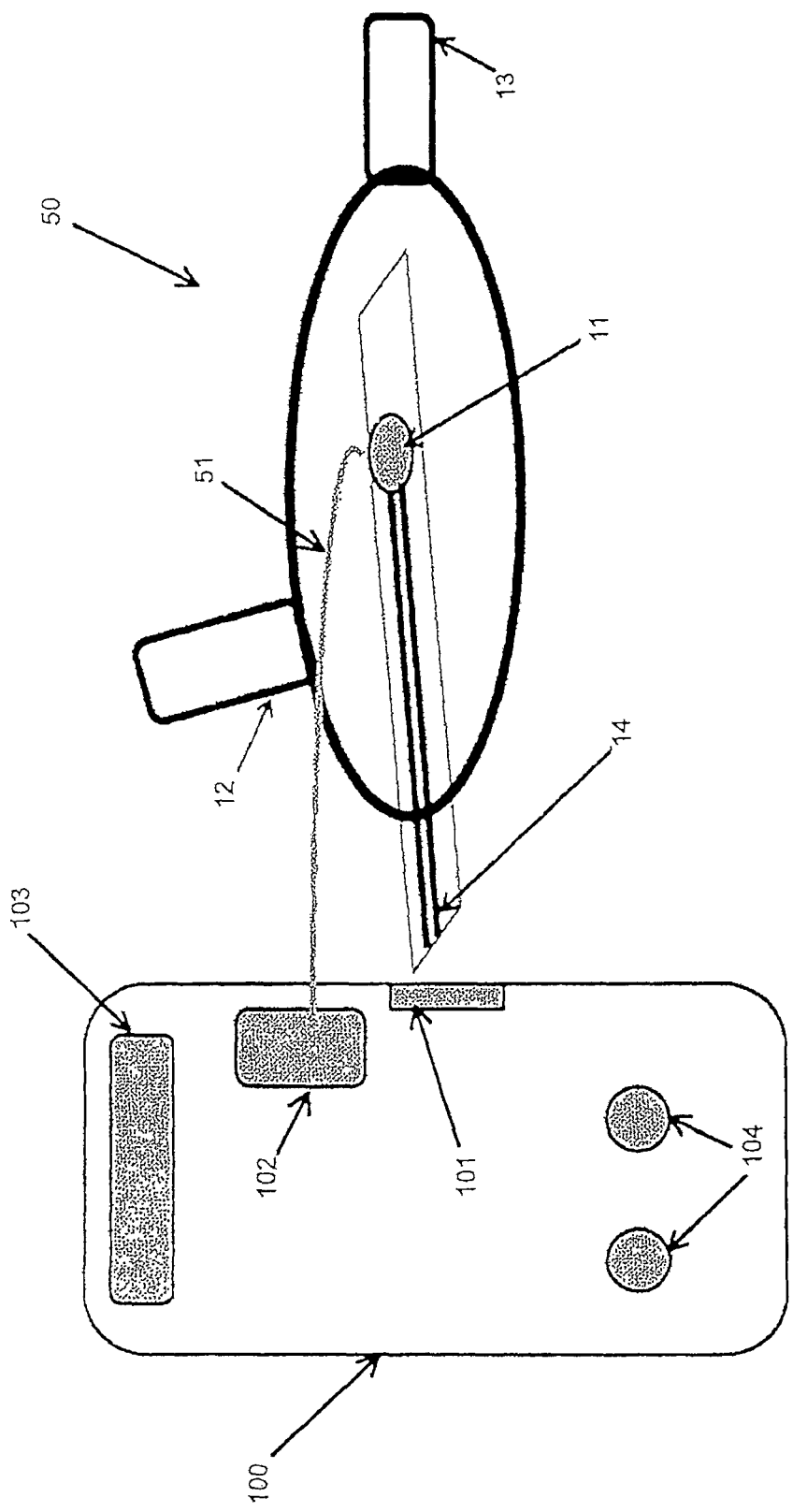
FIG. 5 is a schematic illustration of a mouthpiece with an integrated biosensor with a pump line used to perform liquid delivery to the biosensor according to one embodiment of the invention.

In some embodiments, the hydration process can be fully automated so that hydration occurs with no user intervention. As illustrated in FIG. 5, a mouthpiece 50 can have two separate connections to the electronic analyzer 100, including the electrical connectors 14 and a pump line 51. In addition, the electronic analyzer 100 can include an integrated pump 102. The pump line 51 can be coupled to the pump 102. The pump line 41 can terminate above, below or at some distance from the active area of the biosensor 11. Prior to analysis, the electronic analyzer 100 can automatically perform the hydration process by supplying liquid from the pump 102 in the electronic analyzer 100 through the pump line 51 to hydrate the active area of the biosensor 11. If the pump line 41 terminates below the active area of the biosensor 11, liquid can move to the active area via wetting. If the pump line 41 terminates some distance from the active area, liquid can move to the active area via capillary action. For example, the electronic analyzer 100 can include some sort of computer program that actuates the hydration process, in which pressing a button to begin the analysis starts a timing circuit that actuates the pump 102 at a set time after the button as been pressed. Alternatively, a sensor on the mouthpiece 50 can activate the hydration process. In other embodiments, a pump (not shown) can be housed within the mouthpiece 50.

Some embodiments of the invention include using a liquid sensor so that the hydration material can be detected or the process can be stopped if hydration is not detected. The liquid sensor can ensure delivery of the hydration material. Several different types of liquid sensors can be integrated into the mouthpiece 10 (or 20, 30, 40, or 50), such as an electrode, a polymer, a chemiresistor, a resonant circuit, a transmission line, or an (N)IR laser type sensor.

Some embodiments of the invention can include integrated syringes, sponges, capillaries, nanotubes, polymers, and/or wetting pill strips for purposes of hydrating the biosensor 11. Capillaries or nanotubes can be used to collect moisture from the breath and deposit an appropriate amount on the active area of the biosensor 11. A wetting pull strip can be an adhesive pull-back strip that, when pulled off, leaves moisture in the mouthpiece 10.

Some embodiments of the invention include other sensors or components in order to enhance functionality. The other sensors or components can be integrated directly into the mouthpiece 10 as stand alone items, or can be integrated into the mouthpiece 10 by means of a separate control unit that is coupled electrically and/or mechanically to the mouthpiece 10. Some examples of other sensors include a gas flow sensor, a humidity sensor, a temperature sensor (such as stand-alone or printed thermocouple or thermoresistor), and a gas sensor (such as for oxygen or carbon dioxide to determine alveolar air or breath composition). Sensors can be stand-alone electrode-based sensors. Electrodes can be directly integrated into the mouthpiece 10 by screen or pad printing or plating and can include carbon, gold, platinum, palladium, or ruthenium, among others. Some examples of other components include a heater (such as a printed resistive heater or ceramic heater placed near the active region of the biosensor 11 to help control a chemical reaction taking place), a valve (such as a check valve or manual or automated shutoff valve to isolate the chamber of the mouthpiece 10 housing the biosensor 11), or a baffle (such as a disc or screen to modify the inlet 12 and/or outlet 13 air flow).

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A mouthpiece for use with a portable electronic analyzer for detecting an analyte in a breath sample from an individual, the mouthpiece comprising:

a biosensor that detects the analyte and generates a signal, the biosensor including a chemically active area where a chemical reaction takes place;

a processor, the processor configured to communicate with the biosensor;

a hydration system that is activated by the processor and then causes a plunger to release a liquid to the chemically active area of the biosensor to at least one of enhance, enable, and facilitate the chemical reaction;

a liquid sensor that determines if the liquid was delivered to the chemically active area, the liquid sensor configured to communicate with one or more of the biosensor, the processor, and the hydration system; and hardware that transmits breath analyte data to the electronic analyzer.

2. The mouthpiece of claim 1 wherein the hydration system includes a sack filled with the liquid and at least one of a syringe, a pin, and a roller to puncture the sack to deliver the liquid.

3. The mouthpiece of claim 1 wherein the hydration system includes a pump assembly to deliver the liquid.

4. The mouthpiece of claim 3 wherein the pump assembly can be coupled to the electronic analyzer.

5. The mouthpiece of claim 1 wherein the hydration system includes at least one of a syringe, a sponge, a capillary tube, a nanotube, a polymer, and a wetting pull strip.

6. The mouthpiece of claim 1 wherein the hydration system is configured to deliver the liquid to the chemically active area by at least one of depositing the liquid directly above the chemically active area, depositing the liquid a distance away from the chemically active area, wherein capillary action brings the liquid to the chemically active area, and depositing the liquid below the chemically active area, wherein wetting action brings the liquid to the chemically active area.

7. The mouthpiece of claim 1 wherein the liquid is at least one of water, an acid, a base, a hydrogel, a salt solution, and a neutral buffer.

8. The mouthpiece of claim 1 wherein the liquid contains polymers.

9. The mouthpiece of claim 1 wherein a volume of the liquid is about 0.05 micro-liters to about 100 micro-liters.

10. The mouthpiece of claim 1 wherein the viscosity of the liquid is about 0.1 centipoise to about 200,000 centipoise.

11. The mouthpiece of claim 1 further comprising a chamber housing the biosensor, an inlet receiving the individual's breath into the chamber, and an outlet exhausting the individual's breath out of the chamber.

12. The mouthpiece of claim 1 further comprising a valve positioned in at least one of the inlet and the outlet of the chamber.

13. The mouthpiece of claim 1 and further comprising a heater positioned near the biosensor in order to facilitate the chemical reaction.

* * * * *